(12) United States Patent
Putman et al.

(10) Patent No.: US 11,672,933 B1
(45) Date of Patent: Jun. 13, 2023

(54) METHOD AND SYSTEM FOR BI-LEVEL TREATMENT OF SLEEP APNEA

(71) Applicant: Nanotronics Health, LLC., Brooklyn, NY (US)

(72) Inventors: John B. Putman, Celebration, FL (US); Matthew C. Putman, Brooklyn, NY (US); Julie A. Orlando, Copley, OH (US)

(73) Assignee: Nanotronics Health, LLC., Brooklyn, NY (US)

( * ) Notice: Subject to any disclaimer, the term of this patent is extended or adjusted under 35 U.S.C. 154(b) by 0 days.

(21) Appl. No.: 17/659,971

(22) Filed: Apr. 20, 2022

Related U.S. Application Data

(60) Provisional application No. 63/292,288, filed on Dec. 21, 2021.

(51) Int. Cl.
*A61M 16/00* (2006.01)
*A61M 16/20* (2006.01)
(Continued)

(52) U.S. Cl.
CPC .... *A61M 16/0069* (2014.02); *A61M 16/0003* (2014.02); *A61M 16/024* (2017.08);
(Continued)

(58) Field of Classification Search
CPC .............. A61M 16/00; A61M 16/0057; A61M 16/0066; A61M 16/0069; A61M 16/024;
(Continued)

(56) References Cited

U.S. PATENT DOCUMENTS 9,789,273 B2 10/2017 Lucci et al.
2002/0014239 A1* 2/2002 Chalvignac ......... A61M 16/205
128/204.18
(Continued)

FOREIGN PATENT DOCUMENTS

TW 201529112 8/2015
TW 202146069 12/2021

OTHER PUBLICATIONS

PCT International Application No. PCT/US22/25611, International Search Report and Written Opinion of the International Searching Authority, dated Jul. 27, 2022, 9 pages.
(Continued)

*Primary Examiner* — Joseph D. Boecker
(74) *Attorney, Agent, or Firm* — DLA Piper LLP (US)

(57) ABSTRACT

A positive airway pressure device is disclosed herein. The positive airway pressure device includes a blower, a buffer chamber, a gas manifold, a first sensor, a second sensor, and a controller. The buffer chamber is downstream of the blower. The buffer chamber configured to receive gas generated by the blower and output the gas to a patient. The gas manifold is fluidly coupling the blower to the buffer chamber. The first sensor is at least partially disposed in the gas manifold. The first sensor is configured to measure a first pressure in the gas manifold. The second sensor is at least partially disposed in the buffer chamber. The second sensor is configured to measure a second sensor in the buffer chamber.

15 Claims, 8 Drawing Sheets

(51) Int. Cl.
*G01L 27/00* (2006.01)
*A61M 16/08* (2006.01)
(52) U.S. Cl.
CPC ...... *A61M 16/0858* (2014.02); *A61M 16/203* (2014.02); *G01L 27/002* (2013.01); *A61M 16/0875* (2013.01); *A61M 2016/0018* (2013.01); *A61M 2016/0027* (2013.01); *A61M 2205/70* (2013.01)
(58) Field of Classification Search
CPC ............ A61M 16/0858; A61M 16/202; A61M 16/203; A61M 16/204; A61M 16/205; A61M 2016/0018; A61M 2016/0021; A61M 2016/0024; A61M 2016/0027; A61M 2016/0036; A61M 2205/70; G01L 27/002
See application file for complete search history.

(56) References Cited

U.S. PATENT DOCUMENTS

| | | |
|---|---|---|
| 2005/0005937 A1 | 1/2005 | Farrugia et al. |
| 2006/0272642 A1 | 12/2006 | Chalvignac |
| 2007/0016093 A1 | 1/2007 | Rapoport et al. |
| 2009/0101148 A1* | 4/2009 | Cha .................... A61M 16/024 128/204.22 |
| 2010/0258123 A1 | 10/2010 | Somaiya et al. |
| 2010/0313898 A1 | 12/2010 | Richard et al. |
| 2013/0228180 A1 | 9/2013 | Ahmad et al. |
| 2013/0228181 A1 | 9/2013 | Ahmad et al. |
| 2013/0340758 A1 | 12/2013 | Schindhelm et al. |
| 2014/0069429 A1* | 3/2014 | Lucci .................... A61M 16/20 128/204.21 |
| 2015/0273176 A1 | 10/2015 | Acker et al. |
| 2016/0022938 A1 | 1/2016 | Rapoport et al. |
| 2016/0193438 A1* | 7/2016 | White ................ A61M 16/0069 128/204.23 |
| 2016/0287824 A1 | 10/2016 | Chang |
| 2018/0236191 A1 | 8/2018 | Martin et al. |
| 2020/0179629 A1 | 6/2020 | Burgess et al. |
| 2020/0268994 A1 | 8/2020 | Boulanger |
| 2020/0405986 A1 | 12/2020 | Brambilla et al. |
| 2021/0052839 A1 | 2/2021 | Li et al. |
| 2021/0187221 A1 | 6/2021 | Bassin |

OTHER PUBLICATIONS

PCT International Application No. PCT/US22/29147, International Search Report and Written Opinion of the International Searching Authority, dated Sep. 14, 2022, 16 pages.

* cited by examiner

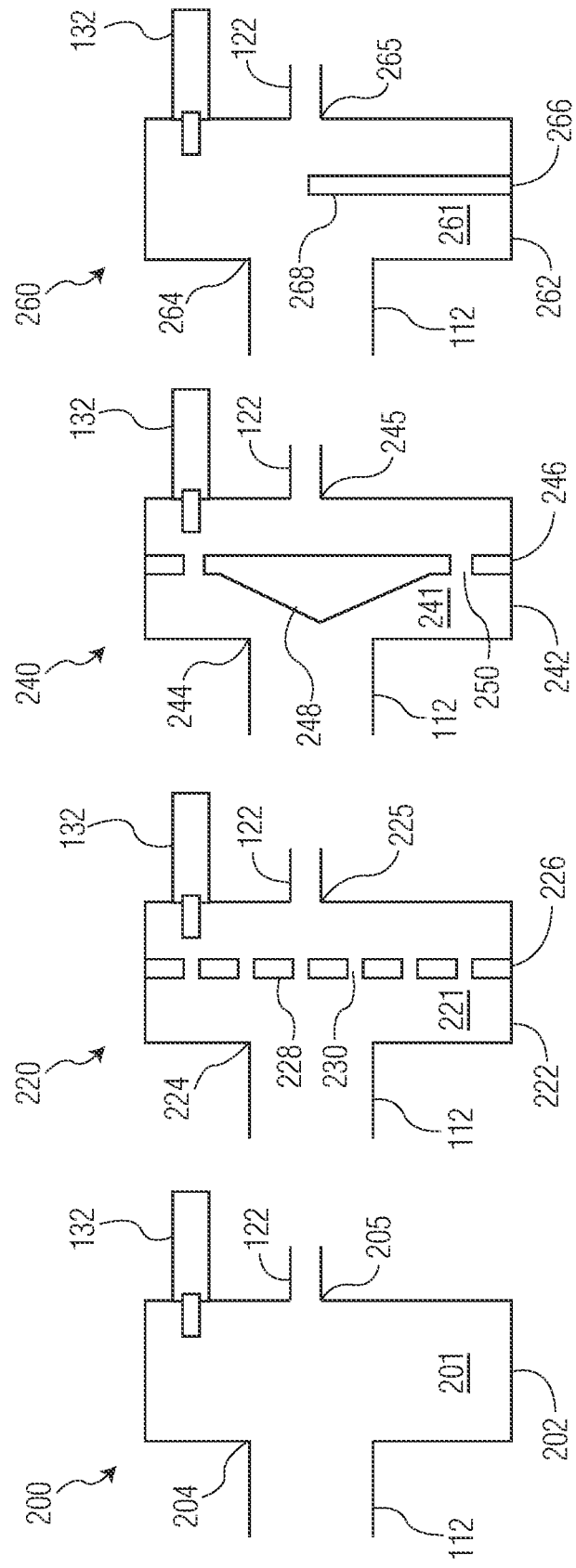

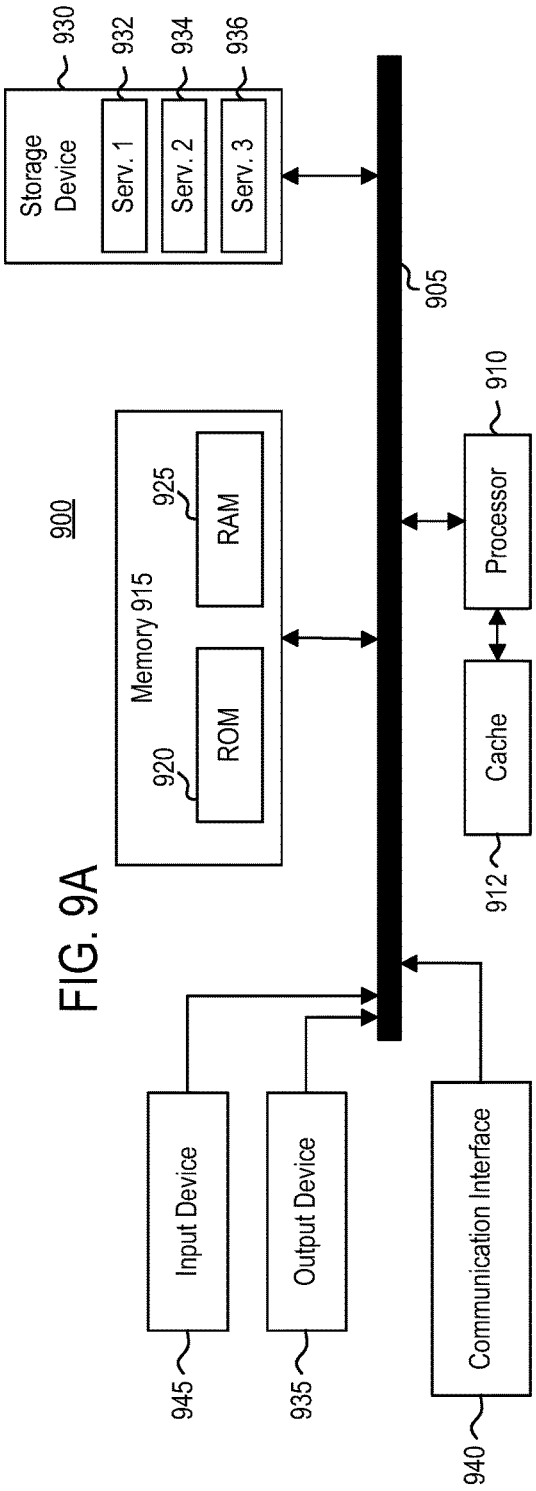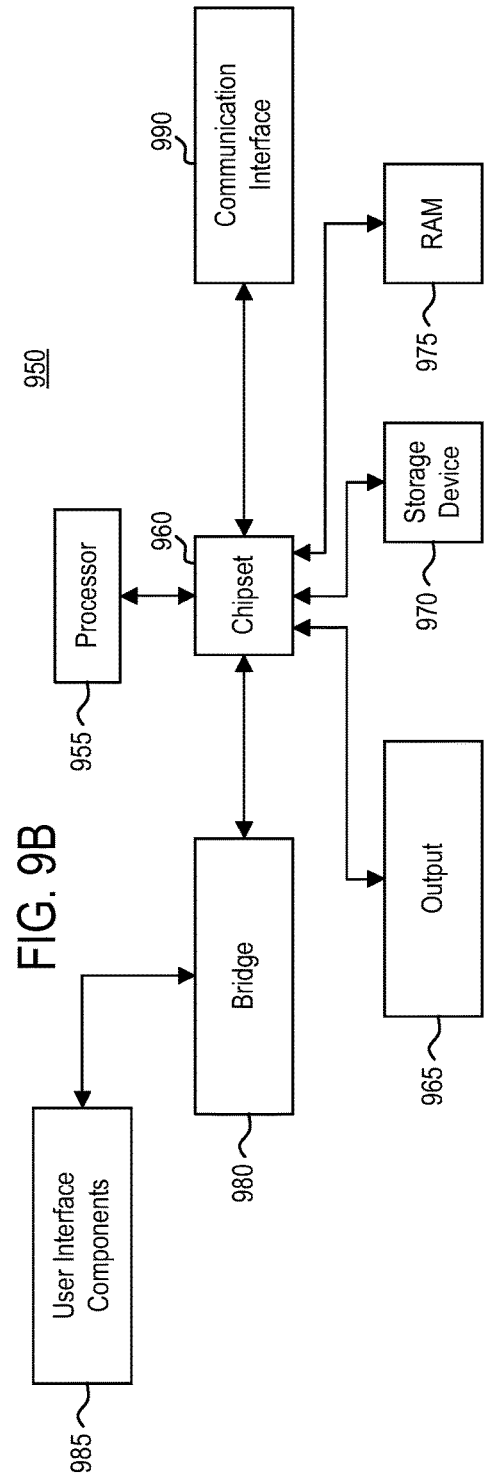

METHOD AND SYSTEM FOR BI-LEVEL TREATMENT OF SLEEP APNEA

CROSS-REFERENCE TO RELATED APPLICATIONS

This application claims priority to U.S. Provisional Application Ser. No. 63/292,288, filed Dec. 21, 2021, which is hereby incorporated by reference in its entirety.

FIELD OF DISCLOSURE

The present disclosure generally relates to a positive airway pressure system, and more specifically, to a system and method for delivering bi-level treatment to a patient using a positive airway pressure system

BACKGROUND

Non-invasive ventilation (NIV) is often used for patients experiencing respiratory destress. This may be prescribed for patients with Obstructive Sleep Apnea (OSA), Chronic obstructive pulmonary disorder (COPD), pneumonia or other respiratory disorders. NIV is often prescribed as supplying positive air pressure (PAP) to the patient by a face mask or other device such as nasal pillows. Depending upon the symptoms, the PAP may be either continuous positive air pressure (CPAP) or bi-level positive air pressure.

SUMMARY

In some embodiments, a positive airway pressure device is disclosed herein. The positive airway pressure device includes a blower, a buffer chamber, a gas manifold, a first sensor, a second sensor, and a controller. The buffer chamber is downstream of the blower. The buffer chamber is configured to receive gas generated by the blower and output the gas to a patient. The gas manifold fluidly couples the blower to the buffer chamber. The first sensor is at least partially disposed in the gas manifold. The first sensor is configured to measure a first pressure in the gas manifold. The second sensor is at least partially disposed in the buffer chamber. The second sensor is configured to measure a second pressure in the buffer chamber. The controller is in communication with the blower, the first sensor, and the second sensor. The controller is configured to perform operations. The operations include initializing the blower to deliver a therapy pressure to the patient during an inhale. The operations further include receiving, from the second sensor, real-time pressure readings while delivering therapy to the patient. The operations further include analyzing the real-time pressure readings to determine that the patient is about to switch from the inhale to an exhale. The operations further include, based on the analyzing, causing the blower to deliver an expiratory pressure to the patient during the exhale. The expiratory pressure is a lower pressure than the therapy pressure.

In some embodiments, a method of delivering therapy to a patient using a positive airway pressure device is disclosed herein. A computing system initializes a blower of the positive airway pressure device to deliver a therapy pressure to a patient during an inhale. The computing system receives, from a second sensor positioned at least partially in a buffer chamber of the positive airway pressure device, real-time pressure readings while delivering therapy to the patient. The computing system analyzes the real-time pressure readings to determine that the patient is about to switch from the inhale to an exhale. Based on the analyzing, the computing system causes the blower to deliver an expiratory pressure to the patient during the exhale. The expiratory pressure is a lower pressure than the therapy pressure.

In some embodiments, a positive airway pressure device is disclosed herein. The positive airway pressure device includes a blower, a buffer chamber, a gas manifold, a first sensor, a second sensor, and a controller. The buffer chamber is downstream of the blower. The buffer chamber is configured to receive gas generated by the blower and output the gas to a patient. The gas manifold fluidly couples the blower to the buffer chamber. The first sensor is at least partially disposed in the gas manifold. The first sensor is configured to measure a first pressure in the gas manifold. The second sensor is at least partially disposed in the buffer chamber. The second sensor is configured to measure a second sensor in the buffer chamber. The controller is in communication with the blower, the first sensor, and the second sensor. The controller is configured to perform operations. The operations include initiating a calibration process for the first sensor. The calibration process configured to reduce differences in readings between the first sensor and the second sensor. The operations further include recording a first plurality of pressure readings from the first sensor and a second plurality of pressure readings from the second sensor. The first plurality of pressure readings and the second plurality of pressure readings are based on a varying amount of pressure delivered to the positive airway pressure device. The operations further include correlating the first plurality of pressure readings with the second plurality of pressure readings. The operations further include calibrating the first sensor based on the correlating.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrated only typical embodiments of this disclosure and are therefore not to be considered limiting of its scope, for the disclosure may admit to other equally effective embodiments.

FIG. 2A illustrates a buffer chamber for use with the PAP device of FIG. 1, according to example embodiments.

FIG. 2B illustrates a buffer chamber for use with the PAP device of FIG. 1, according to example embodiments.

FIG. 2C illustrates a buffer chamber for use with the PAP device of FIG. 1, according to example embodiments.

FIG. 2D illustrates a buffer chamber for use with the PAP device of FIG. 1, according to example embodiments.

FIG. 9A is a block diagram illustrating a computing device, according to example embodiments.

FIG. 9B is a block diagram illustrating a computing device, according to example embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

During CPAP ventilation, a continuous flow of air is supplied to the patient. The typical range of the applied pressure is between 4 and 20 centimeters of water pressure (cm $H_2O$) During bi-level ventilation the pressure is changed between inspiration and expiration so that the pressure is higher during inspiration and then lower during expiration.

During bi-level ventilation for spontaneously breathing patients, it is important for the NIV device to automatically sense when the patient ends their inspiratory cycle and begins expiration. Likewise, it is important for the device to sense the end of the patient's expiration cycle and begins inspiration. Therefore, it is important to algorithmically determine a threshold to instruct, trigger, the device to switch between inspiration and expiration pressures.

During CPAP ventilation some patients find that exhaling against the full pressure of the device is uncomfortable and that it is desirable to lower the pressure during expiration and increase it during inspiration. As with bi-level therapy, the device needs to apply thresholds so that switching between inspiration and expiration pressures occurs automatically.

One or more techniques described herein provides an improvement over conventional system by providing methods for determining the patient specific trigger thresholds for automatically switching between inspiration and expiration pressures for spontaneously breathing patients using PAP devices.

Figure 1:
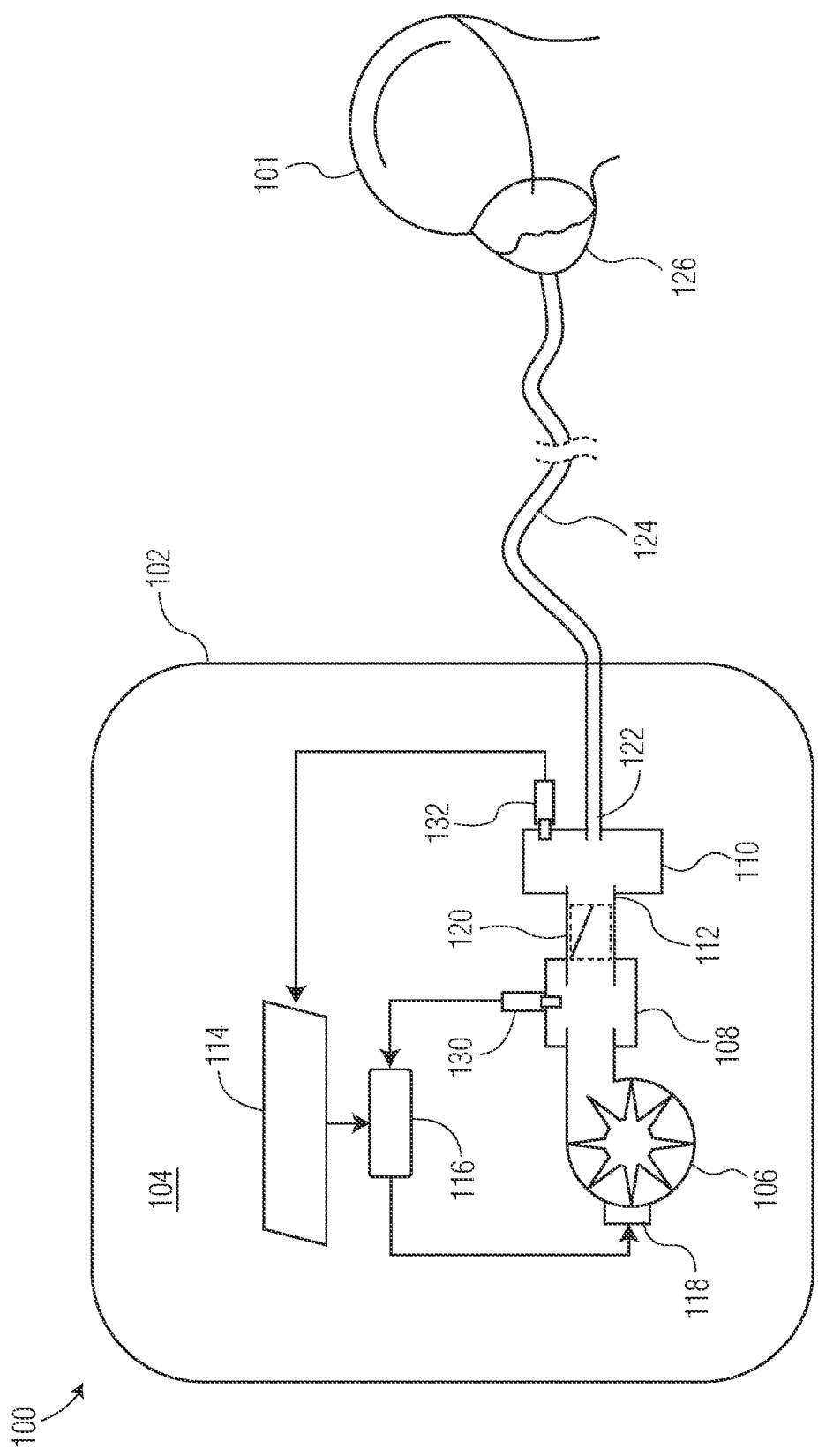
FIG. 1 is a block diagram illustrating a positive airway pressure (PAP) device with interface to a patient, according to example embodiments.

FIG. 1 is a block diagram illustrating a positive airway pressure (PAP) device 100 with interface to a patient 101, according to example embodiments. As shown, PAP device 100 may include a body 102 defining an interior volume 104. PAP device 100 may include a blower 106, a gas manifold 108, a buffer chamber 110, a connector 112, and a microprocessor 114 disposed in interior volume 104.

Blower 106 may be configured to deliver air to gas manifold 108. Blower 106 may include a blower controller 116 associated therewith. Blower controller 116 may be configured to control operation of blower 106. For example, blower controller 116 may be configured to provide electrical input to blower 106 to control a speed of blower 106. For example, blower controller 116 may provide blower 106 with electrical input to obtain a setpoint pressure. In some embodiments, blower controller 116 may provide electrical input to blower terminal block 118 to control speed of blower 106. The speed of blower 106 may be directly related to the maintained pressure.

Gas manifold 108 may be configured to fluidly couple blower 106 with buffer chamber 110. Buffer chamber 110 may be configured to maintain a volume of gas that is removed from blower 106. For example, gas may flow from blower 106, through gas manifold 108, and into buffer chamber 110.

Connector 112 may be configured to couple buffer chamber 110 with gas manifold 108. Connector 112 may provide a flow channel from gas manifold 108 to buffer chamber 110. As shown, in some embodiments, connector 112 may include check valve 120. Check valve 120 may be representative of a one-way valve or gate configured to prevent backflow of gas into blower 106. For example, check valve 120 may be configured to prevent gas at higher pressure from flowing back into blower 106 from buffer chamber 110. If, for example, blower 106 is turned off, check valve 120 may be configured to prevent air from escaping back through blower 106. Such prevention may result in a more consistent control of the delivered pressure and may reduce influence from a patient's respiratory response. In some embodiments, check valve 120 may be designed such that, when blower 106 is turned off, check valve 120 may open a path to external air. Such functionality may ensure that the patient is not asphyxiated in the case of a power failure.

As shown, PAP device 100 may further include a patient connection port 122. Patient connection port 122 may be configured to output gas to a patient delivery system 124. For example, patient connection port 122 may be representative of a port in communication with buffer chamber 110. In operation, patient delivery system 124 may be detachably coupled to PAP device 100. Patient delivery system 124 may be representative of tubing that delivers gas to patient 101 via patient interface 126 (e.g., mask).

PAP device 100 may further include a first sensor 130 and a second sensor 132. First sensor 130 may be positioned proximate blower 106. In some embodiments, such as that shown, first sensor 130 may be at least partially disposed in gas manifold 108. In some embodiments, first sensor 130 may be at least partially disposed in blower 106. Generally, first sensor 130 may be disposed such that it is in close proximity to blower 106. First sensor 130 may be configured to monitor pressure and provide feedback to blower controller 116 such that blower controller 116 can maintain a set pressure. For example, first sensor 130 may send to blower controller 116 a control signal that represents a measured pressured in gas manifold 108. If the setpoint pressure differs from the control signal pressure, blower controller 116 may increase or decrease the speed of blower 106 to maintain the setpoint pressure. In this manner, blower controller 116 may work in conjunction with first sensor 130 to provide a feedback loop for maintaining a desired level of pressure.

Second sensor 132 may be configured to monitor the patient's 101 respiratory cycle. For example, as shown, second sensor 132 may be at least partially disposed in buffer chamber 110. Generally, second sensor 132 may be spaced from first sensor 130. For example, first sensor 130 may be positioned on a first side of connector 112 and second sensor 132 may be positioned on a second side of connector 112. Because second sensor 132 may be configured to monitor pressure that is more directly related to the respiratory response of patient 101, second sensor 132 may inherently be more variable than first sensor 130.

First sensor 130 and second sensor 132 may indicate different pressures depending on the gas flow rate. For example, at a rate of 0.0 l/min (no flow), the difference between first sensor 130 and second sensor 132 is zero. As the flow rate increases, e.g., to 25 l/min, the difference between first sensor 130 and second sensor 132 becomes greater. For this reason, it is useful to calibrate first sensor 130 and second sensor 132 so that they are consistent at any flow rate (e.g., when a patient is spontaneously breathing at a fixed PAP, the average pressures for a given number breathing cycles or for a specified time are the same for first sensor 130 and second sensor 132).

Microprocessor 114 may be configured to control operation of PAP device 100. For example, microprocessor 114 may be configured to control the pressure setpoint of blower 106. In some embodiments, the initial set point of blower 106 may be referred to as the therapy pressure. The therapy pressure may be set by the user or automatically determined by microprocessor 114. The therapy pressure may be delivered to patient 101 when patient 101 inspires.

As those skilled in the art understand, it is often difficult for patients to expire against the therapy pressure. To account for this, microprocessor 114 can dynamically control the pressure delivered to patient 101 during use of PAP device 100. Microprocessor 114 may dynamically control the pressure by detecting the inspiration/expiration cycles of patient 101.

As shown, microprocessor 114 may be in communication with first sensor 130 and/or second sensor 132. In operation, microprocessor 114 may be configured to analyze the patient's 101 respiratory cycle based on data from second sensor 132. For example, microprocessor 114 may use data from second sensor 132 to determine when patient's 101 expiration ends and inspiration begins (upper threshold), and when inspiration ends and expiration begins. In this manner, microprocessor 114 can dynamically adjust the pressure pushing back against patient 101 when patient 101 expires to provide the user with an easier expiration (i.e., patient 101 is not expiring against full pressure). The pressure to which blower output is set when patient 101 is expiring may be referred to as the expiratory pressure. The change between the therapy pressure and the expiratory pressure may be referred to as the pressure drop.

Microprocessor 114 may be configured to receive data from second sensor 132. The data may be presentative of patient's 101 respiratory response. In some embodiments, the data from second sensor 132 is digital and can be interpreted directly by microprocessor 114. In some embodiments, the data from second sensor 132 is analog, in which case microprocessor 114 may convert the analog signal to a digital signal before analysis. Based on the received data, microprocessor 114 may applying one or more techniques to determine if patient 101 is inhaling or exhaling. If inhaling, for example, the data indicates that the lower threshold is met, thus signaling to microprocessor 114 that the patient's inspiration has changed to expiration. If exhaling, for example, the data indicates that the upper threshold is met, thus signaling to microprocessor 114 that the patient's expiration has changed to inspiration.

Based on the respiratory data, microprocessor 114 may adjust the pressure delivered to patient 101. For example, if microprocessor 114 determines that the user is inhaling (e.g., based on the lower threshold being met), then microprocessor 114 may send a control signal to blower controller 116 to set blower controller 116 to the therapy pressure. In another example, if microprocessor 114 determines that the user is exhaling (e.g., based on the upper threshold being met), then microprocessor 114 may send a control signal to blower controller 116 to set blower controller 116 to the expiratory pressure.

In some embodiments, the therapy pressure and the expiratory pressure may be set prior to operation. For example, in a bilevel PAP mode, the therapy pressure and the expiratory pressure delivered to patient 101 may be present by a medical professional. In some embodiments, such as when PAP device 10 is in a CPAP mode with expiratory relief, the continuous pressure (e.g., therapy pressure) may be preset by the medical pressure, and the expiratory pressure may be predefined as reductions in the therapy pressure and may be preset by a medical professional or patient 101. For example, if the continuous pressure is set at 10 cm $H_2O$ and a predefined reduction in pressure of 2 cm $H_2O$ is set, the pressure exerted during exhalation may be 8 cm $H_2O$ Although blower controller 116 and microprocessor 114 are shown as a separate components, those skilled in the art understand that blower controller 116 and microprocessor 114 can be a single computing device.

Microprocessor 114 may be configured to determine the upper threshold and lower threshold through a variety of methods. In some embodiments, microprocessor 114 may calculate the thresholds based on a rate of change of the respiratory response curves. Microprocessor 114 may detect changes in the slopes of the respiratory response curves. For example, the slopes of the respiratory response curves typically approach zero at the end of expiration and inspiration. Using a specific example, the slope of a respiratory response curve at the end of expiration may be around 0.02 cm $H_2O$/sec. If the slope changes negatively by, for example, 0.1 cm $H_2O$/sec, such change may be used as a trigger for microprocessor 114 to change the pressure delivered to patient 101. At the end of inspiration, if the slope of the respiratory response curve changes positively by 0.1 cm $H_2O$/sec, such change can be used as a trigger for microprocessor 114 to change the pressure delivered to patient 101.

In some embodiments, microprocessor 114 may calculate the thresholds based on a determined deviation from maximum pressure (e.g., upper threshold) or pressure deviation from minimum pressure (e.g., lower threshold). For example, in some embodiments, the upper threshold may be predefined as 0.5 cm $H_2O$ above the maximum pressure or the therapy pressure; the lower threshold may be predefined as 0.5 cm $H_2O$ below the minimum pressure.

In some embodiments, microprocessor 114 may be configured to learn a respiratory pattern of patient 101. For example, as discussed above, second sensor 132 may be configured to monitor the pressure change closest to patient 101, while first sensor 130 may be configured to monitor the pressure change within buffer chamber 110, so that the pressure supplied to patient 101 is constant. As those skilled in the art understand, there will be variability between the pressures measured by first sensor 130 and second sensor 132. For example, the pressure readings recorded by second sensor 132 may be more variable, given its proximity to patient 101. To identify a respiratory pattern of patient 101, microprocessor 114 may be configured to subtract the pressure reading of second sensor 132 from the pressure reading of first sensor 130. Such process may eliminate any fluctuations in pressure attributed to blower 106. In this manner, microprocessor 114 may learn the respiratory pattern of the user.

For example, the pressure at first sensor 130 may vary by around +/−0.2 cm $H_2O$, reflecting the control of blower 106. The pressure at second sensor 132 may vary by around +/−0.7 cm $H_2O$, reflecting variation of patient 101, but also including the variation due to motor control of blower 106. Accordingly, the instantaneous difference between pressure readings at first sensor 130 and second sensor 132 may more accurately reflect the inspiratory pattern of patient 101.

FIG. 2A illustrates a buffer chamber 200, according to example embodiments. Buffer chamber 200 may be representative of an embodiment of buffer chamber 110. As shown, buffer chamber 200 may include a body 202 defining an interior volume 201. Buffer chamber 200 may include first opening 204 and a second opening 205. First opening 204 may be configured to receive gas from gas manifold 108 via connector 112. Second opening 205 may be configured to deliver gas to patient delivery system 124 via patient connection port 122. Second sensor 132 may be partially disposed in interior volume 201.

FIG. 2B illustrates a buffer chamber 220, according to example embodiments. Buffer chamber 220 may be representative of an embodiment of buffer chamber 110. As shown, buffer chamber 200 may include a body 222 defining an interior volume 221. Buffer chamber 220 may include first opening 224 and a second opening 225. First opening 224 may be configured to receive gas from gas manifold 108 via connector 112. Second opening 225 may be configured to deliver gas to patient delivery system 124 via patient connection port 122. Second sensor 132 may be partially disposed in interior volume 221.

As shown, buffer chamber 220 may further include a mechanism 226. Mechanism 226 may be representative of a flow restrictor or disruptor. Mechanism 226 may be used to provide backpressure to PAP device 100, as measured by second sensor 132. In the embodiments shown in FIG. 2B, mechanism 226 may be a single plate 228 with a plurality of gas passthrough openings 230.

FIG. 2C illustrates a buffer chamber 240, according to example embodiments. Buffer chamber 240 may be representative of an embodiment of buffer chamber 110. As shown, buffer chamber 240 may include a body 242 defining an interior volume 241. Buffer chamber 240 may include first opening 244 and a second opening 245. First opening 244 may be configured to receive gas from gas manifold 108 via connector 112. Second opening 245 may be configured to deliver gas to patient delivery system 124 via patient connection port 122. Second sensor 132 may be partially disposed in interior volume 241.

As shown, buffer chamber 240 may further include a mechanism 246. Mechanism 246 may be representative of a flow restrictor or disruptor. Mechanism 246 may be used to provide backpressure to PAP device 100, as measured by second sensor 132. In the embodiments shown in FIG. 2C, mechanism 246 may be a cone 248 with a gas passthrough openings 250 at the base of cone 248.

FIG. 2D illustrates a buffer chamber 260, according to example embodiments. Buffer chamber 260 may be representative of an embodiment of buffer chamber 110. As shown, buffer chamber 260 may include a body 262 defining an interior volume 261. Buffer chamber 260 may include first opening 264 and a second opening 265. First opening 264 may be configured to receive gas from gas manifold 108 via connector 112. Second opening 265 may be configured to deliver gas to patient delivery system 124 via patient connection port 122. Second sensor 132 may be partially disposed in interior volume 261.

As shown, buffer chamber 260 may further include a mechanism 266. Mechanism 266 may be representative of a flow restrictor or disruptor. Mechanism 266 may be used to provide backpressure to PAP device 100, as measured by second sensor 132. In the embodiments shown in FIG. 2D, mechanism 266 may be a single plate 268 that covers half of the gas pathway.

Figure 4:
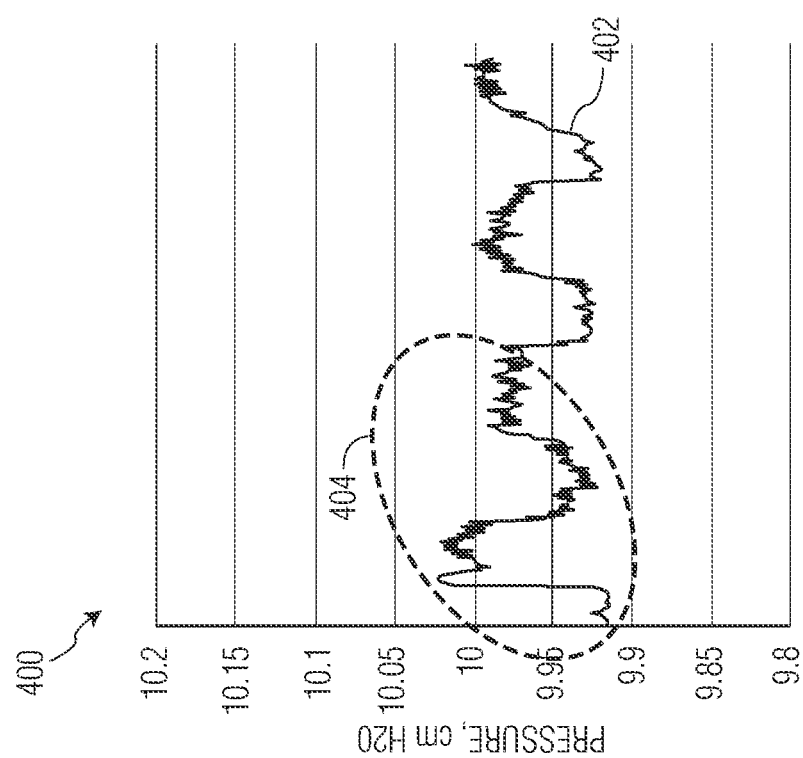
FIG. 4 is a chart illustrating patient respiratory response measured by second sensor, according to example embodiments.
Figure 3:
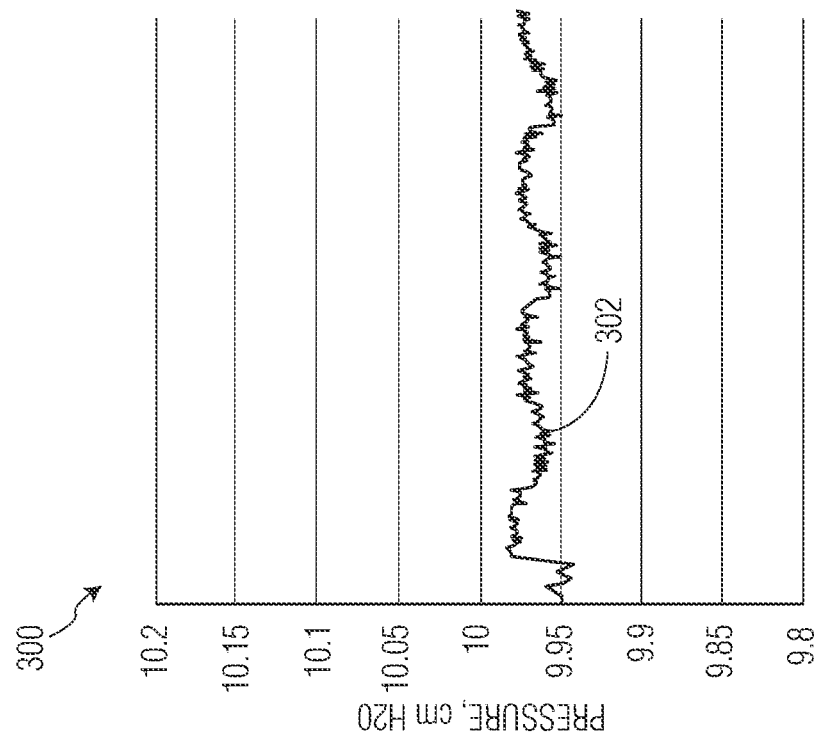
FIG. 3 is a chart illustrating patient respiratory response measured by first sensor, according to example embodiments.

FIG. 3 is a chart 300 illustrating patient respiratory response 302 measured by first sensor 130, according to example embodiments. FIG. 4 is a chart illustrating patient respiratory response 402 measured by second sensor 132, according to example embodiments. As clear from a comparison of chart 300 to chart 400, the pressure as measured by second sensor 132 is more variable than the pressure as measured by first sensor 130. This is attributed to second sensor 132 being closer to patient 101 than first sensor 130.

Figure 5:
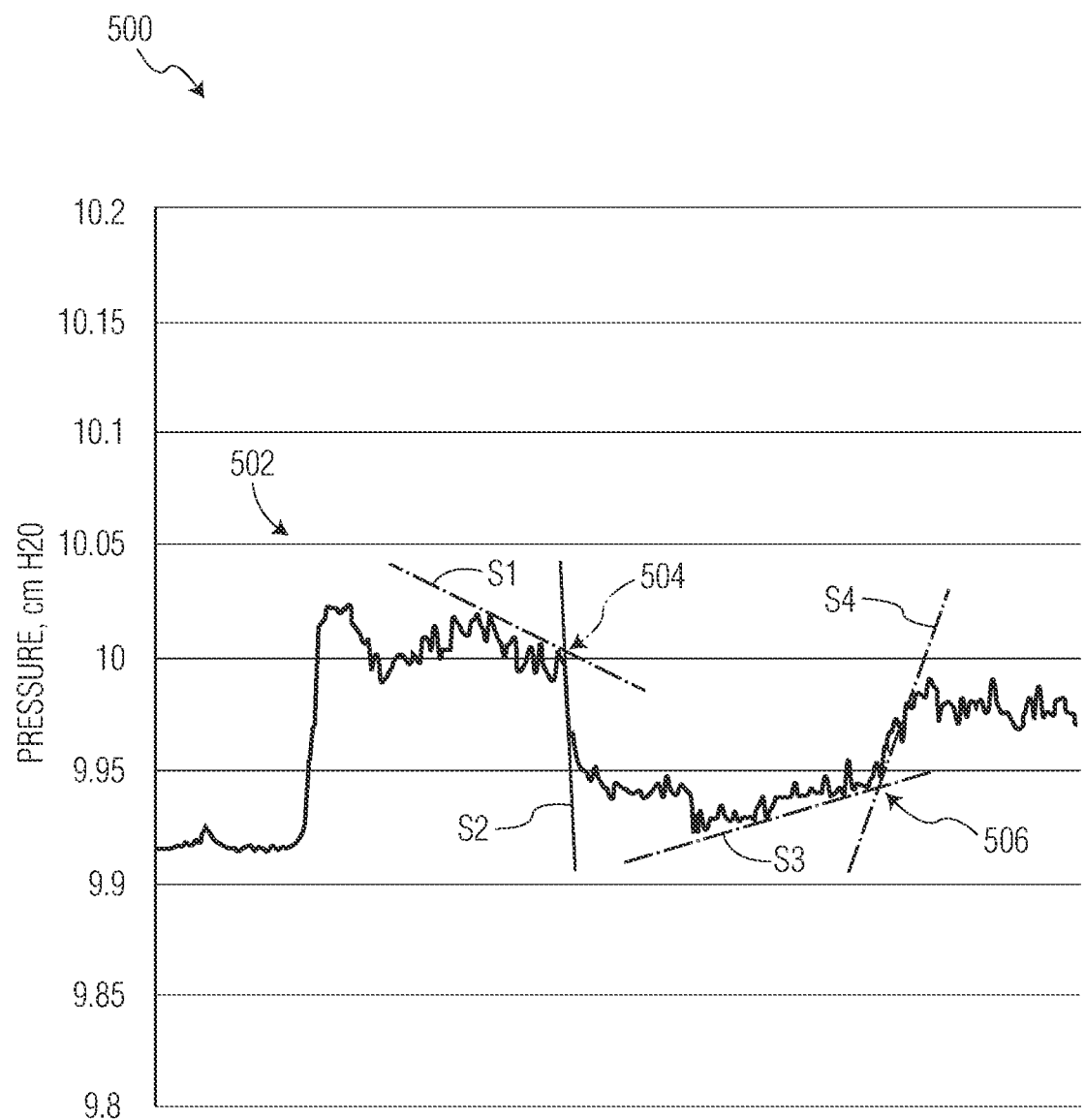
FIG. 5 is a chart illustrating portion of the chart of FIG. 4 in more detail, according to example embodiments.

FIG. 5 is a chart 500 illustrating portion 404 of chart 400 in more detail, according to example embodiments. As shown in FIG. 4, a portion 404 of chart 400 is emphasized. Portion 404 may be referred to as patient respiratory response curve 502. When determining whether a user is inhaling or exhaling, microprocessor 114 may determine if an upper threshold 504 or lower threshold 506 is met.

Microprocessor 114 may calculate a first slope (S1) of respiratory response curve 502 at the end of respiration. Microprocessor 114 may calculate slope S1 over several seconds in real-time. Microprocessor 114 may calculate a second slope (S2) of respiratory response curve 502 at the end of respiration and after inspiration begins. Microprocessor 114 can calculate second slope (S2) continuously, in real-time, and in fractional seconds. Microprocessor 114 may calculate upper threshold 504 in real-time and can immediately trigger a change in the pressure.

Microprocessor 114 may calculate a third slope (S3) of respiratory response curve 502 at the end of inspiration. Microprocessor 114 may calculate third slope (S3) over several seconds in real-time. Microprocessor 114 may calculate a second slope (S4) of respiratory response curve 502 at the end of inspiration and after expiration begins. Microprocessor 114 can calculate second slope (S4) continuously, in real-time, and in fractional seconds. Microprocessor 114 may calculate lower threshold 506 in real-time and can immediately trigger a change in the pressure.

Figure 6:
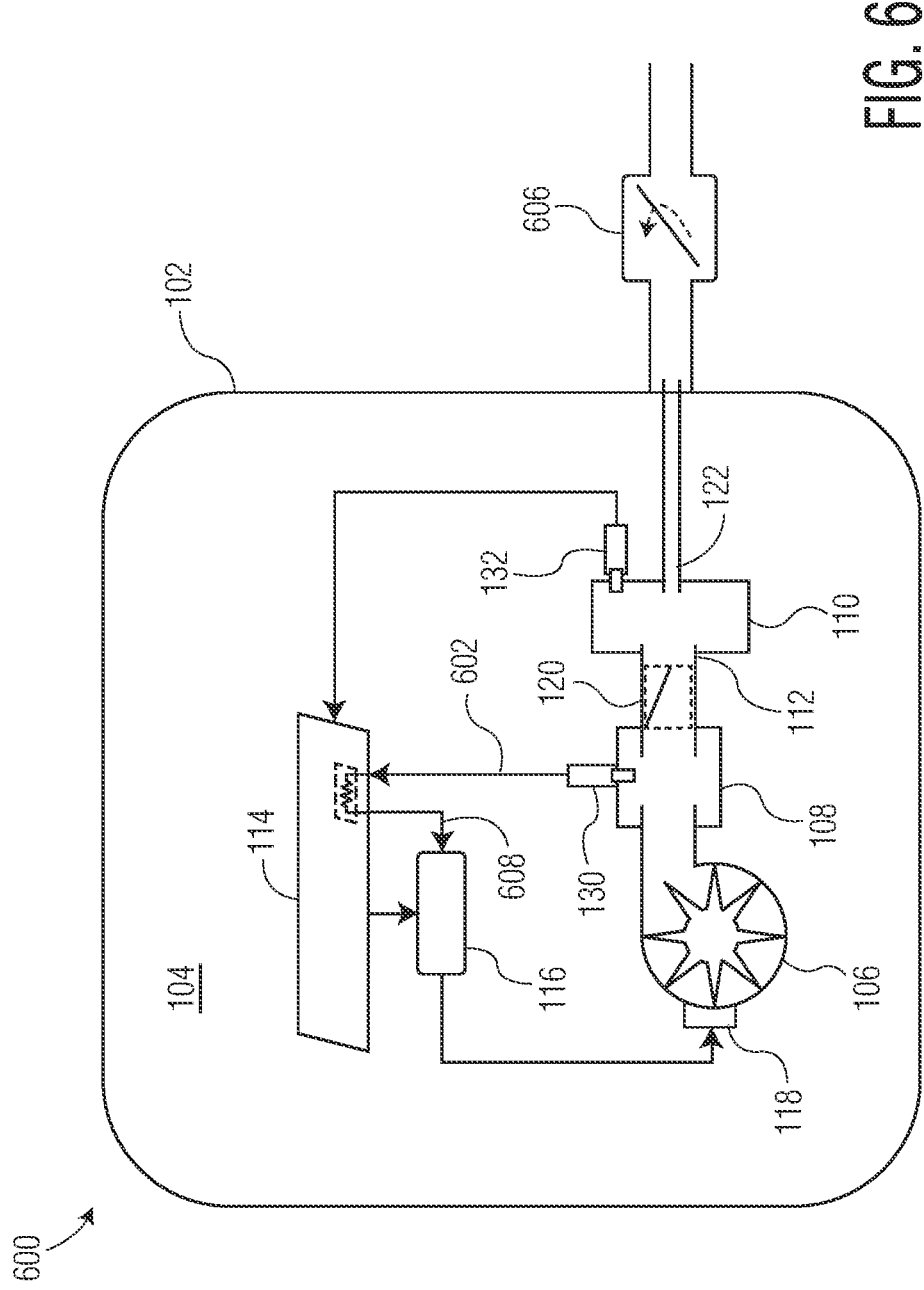
FIG. 6 illustrates an example how first sensor of PAP device may be calibrated, according to example embodiments.

FIG. 6 is a block diagram illustrating PAP device 600, according to example embodiments. PAP device 600 is substantially similar to PAP device 100. PAP device 600 illustrates a flow of data when during a calibration process.

As described above, the difference between the pressure at first sensor 130 less the pressure at second sensor 132 more directly relates to the patient's respiratory response. There is often a difference between pressures at second sensor 132 and first sensor 130. For example, if system is closed, i.e., there is no gas flow, the pressure measured at first sensor 130 is the same as the pressure measured at second sensor 132. As the airflow increases, the difference between the pressures measured at first sensor 130 and second sensor 132 becomes greater. To account for this, first sensor 130 may undergo a calibration process so that the differences are eliminated or reduced.

FIG. 6 illustrates an example how first sensor 130 of PAP device 600 may be calibrated, according to example embodiments. PAP device 600 may be substantially similar to PAP device 100. During such process, output 602 from first sensor 130 may be sent to the microprocessor 114. To begin calibration, microprocessor 114 may set the therapy setpoint to the maximum pressure of the PAP device 600.

In some embodiments, during calibration, PAP device 600 may be connected to an adjustable valve 606. Valve 606 may be closed fully at the start of calibration so that there is no air flow through PAP device 600. Valve 606 may be incrementally opened. At each increment, microprocessor 114 may record pressure readings from first sensor 130 and second sensor 132. This process may continue until valve 606 is fully open. To calibrate sensor 130 and sensor 132, microprocessor 114 may correlate the two pressures and output a calibrated control signal 608 to the blower controller 116. Although not shown, PAP device 600 may further be connected to a flow meter.

For example, at each point of calibration, valve 606 may be opened incrementally. In some embodiments, there is a minimum of four increments at which sensor 130 and sensor 132 may record pressure measurements. At each increment, microprocessor 114 may receive two values: a first pressure as measured by sensor 132 (e.g., the desired or therapy pressure) and a second pressure as measured by sensor 130 (e.g., the blower control pressure). Because microprocessor 114 outputs the therapy pressure to blower controller 116, it is beneficial that the pressure at first sensor 130 be "calibrated" to substantially the same pressure as that measured by second sensor 132. If, for example, the correlation between the pressure measured at second sensor 132 and the pressure measured at first sensor 130 was linear, then a linear correlation, e.g., $y=mx+b$, may be used, where x represents the pressure at second sensor 132 and y represents the calibrated pressure at first sensor 130. For example, if $m=1.005$ and $b=0$, then, if the therapy pressure as measured by second sensor 132 is set to be 10 cm $H_2O$, the set pressure output to blower controller 116 may be 10.05. Accordingly, at a high flow rate, second sensor 132 may read lower than the set pressure to blower controller 116 if not calibrated. To compensate for this difference, the set pressure would need to be higher.

Figure 7:
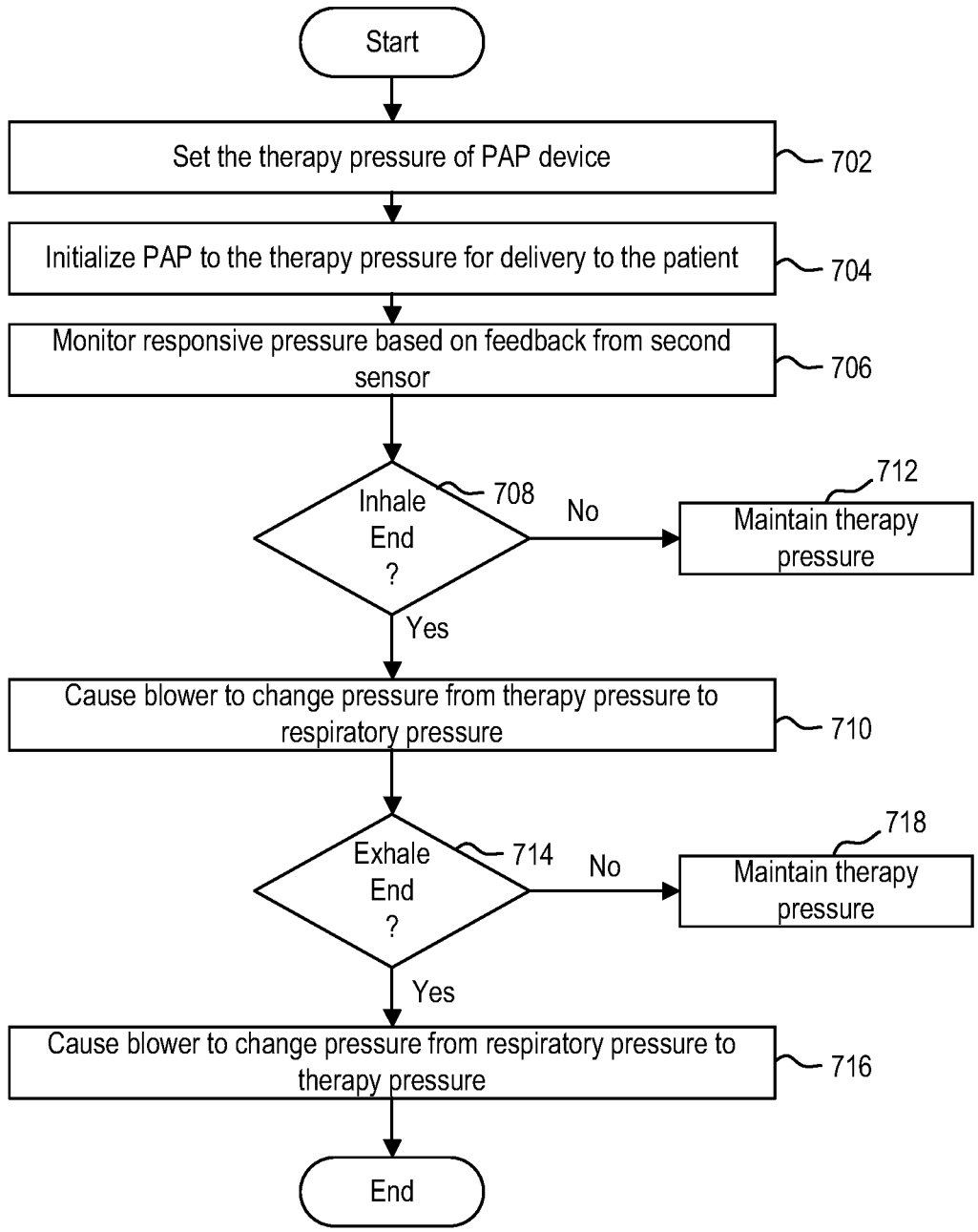
FIG. 7 is a flow diagram illustrating a method of administering therapy with PAP device, according to example embodiments.

FIG. 7 is a flow diagram illustrating a method 700 of administering therapy with PAP device 100, according to example embodiments. Method 700 may begin at step 702.

At step 702, microprocessor 114 may set the therapy pressure of PAP device 100. In some embodiments, the therapy pressure may be input to microprocessor 114 via a user interface associated with microprocessor 114. In some embodiments, the therapy pressure may be input to microprocessor 114 via an external device (e.g., a mobile device of patient 101) over a wired or wireless connection (e.g., Bluetooth, ZigBee, Wifi, etc.). In some embodiments, the therapy pressure may be automatically determined by microprocessor 114.

At step 704, microprocessor 114 may initialize PAP device 100 to the therapy pressure for delivery to patient 101. For example, microprocessor 114 may provide a signal to blower controller 116 to set a speed of blower 106 to maintain the determined therapy pressure. The signal to blower controller 116 from microprocessor 114 may cause blower controller 116 to output a blower output signal to terminal block 118 to control a speed of blower 106, such that blower 106 produces the therapy pressure.

At step 706, microprocessor 114 may monitor responsive pressure based on feedback from second sensor 132. For example, microprocessor 114 may receive real-time pressure readings from second sensor 132 as PAP device 100 delivers the therapy pressure to patient 101. Microprocessor 114 may analyze the real-time pressure readings to determine when to adjust the pressure delivered to patient 101. For example, microprocessor 114 may dynamically adjust the pressure delivered to the patient 101 based on a determination as to whether patient 101 is exhaling or inhaling.

At step 708, microprocessor 114 may determine whether patient 101 is about to stop inhaling based on the monitored responsive pressure. For example, microprocessor 114 may receive respiratory data from second sensor 132. In some embodiments, the respiratory data may be representative of a measure of pressure over time. Microprocessor 114 may analyze the respiratory data to identify a lower threshold.

If, at step 708, microprocessor 114 determines that an inspiratory threshold has been met (i.e., patient 101 has hit the lower threshold), then this may indicate to microprocessor 114 that the patient's inspiration has changed or is about to change to expiration. Accordingly, at step 710, microprocessor 114 may change the pressure (e.g., lower the pressure) delivered to the user to the expiration pressure. In some embodiments, changing the pressure delivered to the user may include microprocessor 114 sending a signal to blower controller 116 or block terminal block 118 to cause blower controller 116 or block terminal block 118 to adjust to speed of blower 106 to achieve the expiration pressure.

If, however, at step 708, microprocessor 114 determines that patient 101 is not about to stop inhaling, then, at step 712, microprocessor 114 may maintain the pressure therapy.

At step 714, microprocessor 114 may determine whether patient 101 is about to stop exhaling based on the monitored responsive pressure. For example, microprocessor 114 may receive respiratory data from second sensor 132. In some embodiments, the respiratory data may be representative of a measure of pressure over time. Microprocessor 114 may analyze the respiratory data to identify an upper threshold.

If, at step 714, microprocessor 114 determines that an expiratory threshold has been met (i.e., patient 101 has hit the upper threshold), then this may indicate to microprocessor 114 that the patient's expiration has changed or is about to change to inspiration. Accordingly, at step 716, microprocessor 114 may change the pressure delivered to the user to the therapy pressure. In some embodiments, changing the pressure delivered to the user may include microprocessor 114 sending a signal to blower controller 116 or block terminal block 118 to cause blower controller 116 or block terminal block 118 to adjust to speed of blower 106 to achieve the therapy pressure.

If, however, at step 714, microprocessor 114 determines that patient 101 is not about to stop exhaling, then, at step 718, microprocessor 114 may maintain the pressure therapy.

Such switching between therapy pressure and expiratory pressure may continue until therapy has concluded.

Figure 8:
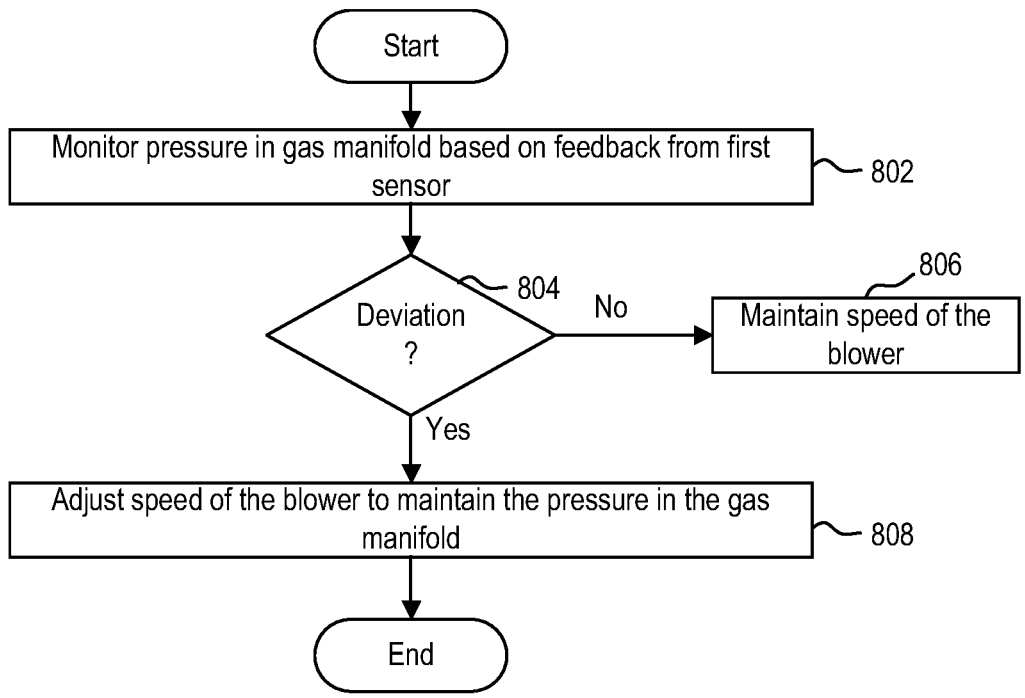
FIG. 8 is a flow diagram illustrating a method of administering therapy with PAP device, according to example embodiments.

FIG. 8 is a flow diagram illustrating a method 800 of administering therapy with PAP device 100, according to example embodiments. Method 800 may begin at step 802.

At step 802, blower controller 116 may monitor pressure in gas manifold 108 based on feedback from first sensor 130. For example, microprocessor 114 may receive real-time pressure readings from first sensor 130 as PAP device 100 delivers the therapy pressure to patient 101. Microprocessor 114 may analyze the real-time pressure readings to determine when to adjust the pressure such that the current pressure setpoint is maintained. For example, microprocessor 114 may dynamically adjust the speed of blower 106, such that the pressure in gas manifold 108 remains consistent.

At step 804, blower controller 116 may determine whether the pressure in gas manifold 108 deviated at a threshold amount from the setpoint pressure (e.g., therapy pressure, expiratory pressure, etc.) based on pressure readings from first sensor 130.

If, at step 804, blower controller 116 determines that the pressure in gas manifold 108 is consistent (e.g., the pressure does not deviate a threshold amount from the setpoint pressure), then at step 806 blower controller 116 may maintain the speed of blower 106. In other words, blower controller 116 may not adjust the speed of blower 106.

If, however, at step 804, blower controller 116 determines that the pressure in gas manifold 108 is not consistent (e.g., the pressure in gas manifold 108 has deviated a threshold amount from the setpoint pressure), then at step 808 blower controller 116 may adjust the speed of blower 106 so that the setpoint pressure is once again achieved. In some embodiments, controller 116 may send a blower controller output signal to terminal block 118 to adjust the speed of blower 106.

Such monitoring may continue until therapy has concluded.

FIG. 9A illustrates a system bus architecture of computing system 900, according to example embodiments. System 900 may be representative of at least a portion of microprocessor 114 and/or blower controller 116. One or more components of system 900 may be in electrical communication with each other using a bus 905. System 900 may include a processing unit (CPU or processor) 910 and a system bus 905 that couples various system components including the system memory 915, such as read only memory (ROM) 920 and random access memory (RAM) 925, to processor 910. System 900 may include a cache of high-speed memory connected directly with, in close proximity to, or integrated as part of processor 910. System 900 may copy data from memory 915 and/or storage device 930 to cache 912 for quick access by processor 910. In this way, cache 912 may provide a performance boost that avoids processor 910 delays while waiting for data. These and other modules may control or be configured to control processor 910 to perform various actions. Other system memory 915 may be available for use as well. Memory 915 may include multiple different types of memory with different performance characteristics. Processor 910 may include any general purpose processor and a hardware module or software module, such as service 1 932, service 2 934, and service 3 936 stored in storage device 930, configured to control processor 910 as well as a special-purpose processor where software instructions are incorporated into the actual processor design. Processor 910 may essentially be a completely self-contained computing system, containing multiple cores or processors, a bus, memory controller, cache, etc. A multi-core processor may be symmetric or asymmetric.

To enable user interaction with the computing system 900, an input device 945 may represent any number of input mechanisms, such as a microphone for speech, a touch-sensitive screen for gesture or graphical input, keyboard, mouse, motion input, speech and so forth. An output device 935 may also be one or more of a number of output mechanisms known to those of skill in the art. In some instances, multimodal systems may enable a user to provide multiple types of input to communicate with computing system 900. Communications interface 940 may generally govern and manage the user input and system output. There is no restriction on operating on any particular hardware arrangement and therefore the basic features here may easily be substituted for improved hardware or firmware arrangements as they are developed.

Storage device 930 may be a non-volatile memory and may be a hard disk or other types of computer readable media which may store data that are accessible by a computer, such as magnetic cassettes, flash memory cards, solid state memory devices, digital versatile disks, cartridges, random access memories (RAMs) 925, read only memory (ROM) 920, and hybrids thereof.

Storage device 930 may include services 932, 934, and 936 for controlling the processor 910. Other hardware or software modules are contemplated. Storage device 930 may be connected to system bus 905. In one aspect, a hardware module that performs a particular function may include the software component stored in a computer-readable medium in connection with the necessary hardware components, such as processor 910, bus 905, output device 935 (e.g., display), and so forth, to carry out the function.

FIG. 9B illustrates a computer system 950 having a chipset architecture that may represent at least a portion of microprocessor 114 and/or blower controller 116. Computer system 950 may be an example of computer hardware, software, and firmware that may be used to implement the disclosed technology. System 950 may include a processor 955, representative of any number of physically and/or logically distinct resources capable of executing software, firmware, and hardware configured to perform identified computations. Processor 955 may communicate with a chipset 960 that may control input to and output from processor 955. In this example, chipset 960 outputs information to output 965, such as a display, and may read and write information to storage device 970, which may include magnetic media, and solid state media, for example. Chipset 960 may also read data from and write data to storage device 975 (e.g., RAM). A bridge 980 for interfacing with a variety of user interface components 985 may be provided for interfacing with chipset 960. Such user interface components 985 may include a keyboard, a microphone, touch detection and processing circuitry, a pointing device, such as a mouse, and so on. In general, inputs to system 950 may come from any of a variety of sources, machine generated and/or human generated.

Chipset 960 may also interface with one or more communication interfaces 990 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 955 analyzing data stored in storage device 970 or storage device 975. Further, the machine may receive inputs from a user through user interface components 985 and execute appropriate functions, such as browsing functions by interpreting these inputs using processor 955.

It may be appreciated that example systems 900 and 950 may have more than one processor 910 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

The invention claimed is:

1. A positive airway pressure device, comprising:
a blower;
a buffer chamber downstream of the blower, the buffer chamber configured to receive gas generated by the blower and output the gas to a patient, the buffer chamber comprising a mechanism configured to provide backpressure to the positive airway pressure device, wherein the mechanism is at least one of:
a single plate with a plurality of gas passthrough openings formed therethrough,
a cone with a gas passthrough opening formed at a base of the cone, or
a single plate that covers half of a gas pathway through the buffer chamber;
a gas manifold fluidly coupling the blower to the buffer chamber;
a first sensor at least partially disposed in the gas manifold, the first sensor configured to measure a first pressure in the gas manifold;
a second sensor at least partially disposed in the buffer chamber, the second sensor configured to measure a second pressure in the buffer chamber; and
a controller in communication with the blower, the first sensor, and the second sensor, the controller configured to perform operations, comprising:
initializing the blower to deliver a therapy pressure to the patient during an inhale;
receiving, from the second sensor, real-time pressure readings while delivering therapy to the patient;
analyzing the real-time pressure readings to determine that the patient is about to switch from the inhale to an exhale; and
based on the analyzing, causing the blower to deliver an expiratory pressure to the patient during the exhale, the expiratory pressure being a lower pressure than the therapy pressure.

2. The positive airway pressure device of claim 1, further comprising:
receiving, from the first sensor, a gas manifold pressure reading during delivery of the expiratory pressure to the patient;
determining, based on the gas manifold pressure reading, that an internal pressure in the gas manifold has deviated a threshold amount from the expiratory pressure; and
based on the determining, adjusting a speed of the blower to maintain the expiratory pressure.

3. The positive airway pressure device of claim 1, further comprising:
receiving, from the second sensor, additional real-time pressure readings while delivering the expiratory pressure to the patient;
analyzing the additional real-time pressure readings to determine that the patient is about to switch from the exhale to a second inhale; and
based on the analyzing, causing the blower to deliver the therapy pressure to the patient during the second inhale.

4. The positive airway pressure device of claim 3, further comprising:
receiving, from the first sensor, a gas manifold pressure reading during delivery of the therapy pressure to the patient;
determining, based on the gas manifold pressure reading, that an internal pressure in the gas manifold has deviated a threshold amount from the therapy pressure; and
based on the determining, adjusting a speed of the blower to maintain the therapy pressure.

5. The positive airway pressure device of claim 3, wherein analyzing the real-time pressure readings to determine that the patient is about to switch from the inhale to the exhale comprises:
determining that a pressure reading from the second sensor has hit an upper threshold indicative of a switch between the exhale to the second inhale.

6. The positive airway pressure device of claim 1, wherein analyzing the real-time pressure readings to determine that the patient is about to switch from the inhale to the exhale comprises:
determining that a pressure reading from the second sensor has hit a lower threshold indicative of a switch between the inhale to the exhale.

7. A method of delivering therapy to a patient using a positive airway pressure device, the method comprising:
initializing, by a computing system, a blower of the positive airway pressure device to deliver a therapy pressure to a patient during an inhale;
receiving, by the computing system from a second sensor positioned at least partially in a buffer chamber of the positive airway pressure device, real-time pressure readings while delivering therapy to the patient;
analyzing, by the computing system, the real-time pressure readings to determine that the patient is about to switch from the inhale to an exhale;
based on the analyzing, causing, by the computing system, the blower to deliver an expiratory pressure to the patient during the exhale, the expiratory pressure being a lower pressure than the therapy pressure;
receiving, by the computing system from a first sensor positioned in a gas manifold upstream of the buffer chamber and downstream of the blower, a gas manifold pressure reading during delivery of the expiratory pressure to the patient;
determining, by the computing system, based on the gas manifold pressure reading, that an internal pressure in the gas manifold has deviated a threshold amount from the expiratory pressure; and
based on the determining, adjusting, by the computing system, a speed of the blower to maintain the expiratory pressure.

8. The method of claim 7, further comprising:
receiving, by the computing system from the second sensor, additional real-time pressure readings while delivering the expiratory pressure to the patient;
analyzing, by the computing system, the additional real-time pressure readings to determine that the patient is about to switch from the exhale to a second inhale; and
based on the analyzing, causing, by the computing system, the blower to deliver the therapy pressure to the patient during the second inhale.

9. The method of claim 8, further comprising:
receiving, by the computing system from the first sensor positioned in the gas manifold upstream of the buffer chamber and downstream of the blower, a second gas manifold pressure reading during delivery of the therapy pressure to the patient;
determining, by the computing system, based on the second gas manifold pressure reading, that the internal pressure in the gas manifold has deviated the threshold amount from the therapy pressure; and
based on the determining, adjusting, by the computing system, the speed of the blower to maintain the therapy pressure.

10. The method of claim 8, wherein analyzing, by the computing system, the real-time pressure readings to determine that the patient is about to switch from the inhale to the exhale comprises:
determining that a pressure reading from the second sensor has hit an upper threshold indicative of a switch between the exhale to the second inhale.

11. The method of claim 7, wherein analyzing, by the computing system, the real-time pressure readings to determine that the patient is about to switch from the inhale to the exhale comprises:
determining that a pressure reading from the second sensor has hit a lower threshold indicative of a switch between the inhale to the exhale.

12. The method of claim 7, further comprising:
initiating, by the computing system, an offline calibration process for the first sensor positioned in the gas manifold upstream of the buffer chamber and downstream of the blower, the offline calibration process configured to reduce differences in readings between the first sensor and the second sensor;
recording, by the computing system, a first plurality of pressure readings from the first sensor and a second plurality of pressure readings from the second sensor, the first plurality of pressure readings and the second plurality of pressure readings based on a varying amount of pressure delivered to the positive airway pressure device;
correlating, by the computing system, the first plurality of pressure readings with the second plurality of pressure readings; and
calibrating, by the computing system, the first sensor based on the correlating.

13. A positive airway pressure device, comprising:
a blower;
a buffer chamber downstream of the blower, the buffer chamber configured to receive gas generated by the blower and output the gas to a patient;
a gas manifold fluidly coupling the blower to the buffer chamber;
a first sensor at least partially disposed in the gas manifold, the first sensor configured to measure a first pressure in the gas manifold;
a second sensor at least partially disposed in the buffer chamber, the second sensor configured to measure a second pressure in the buffer chamber; and
a controller in communication with the blower, the first sensor, and the second sensor, the controller configured to perform operations, comprising:
initiating a calibration process for the first sensor, the calibration process configured to reduce differences in readings between the first sensor and the second sensor;
recording a first plurality of pressure readings from the first sensor and a second plurality of pressure readings from the second sensor, the first plurality of pressure readings and the second plurality of pressure readings based on a varying amount of pressure delivered to the positive airway pressure device;
correlating the first plurality of pressure readings with the second plurality of pressure readings; and
calibrating the first sensor based on the correlating.

14. The positive airway pressure device of claim 13, wherein the positive airway pressure device is coupled with an adjustable valve.

15. The positive airway pressure device of claim 14, wherein recording the first plurality of pressure readings from the first sensor and the second plurality of pressure readings from the second sensor comprises:
recording a first pressure reading from the first sensor and a second pressure reading form the second sensor for each position of the adjustable valve between fully opened and fully closed.

* * * * *